United States Patent [19]

Fukuda

[11] 4,257,708

[45] Mar. 24, 1981

[54] APPARATUS FOR MEASURING THE DEGREE OF RINSING

[75] Inventor: Norisuke Fukuda, Tokyo, Japan

[73] Assignee: Tokyo Shibaura Denki Kabushiki Kaisha, Kawasaki, Japan

[21] Appl. No.: 31,738

[22] Filed: Apr. 20, 1979

[30] Foreign Application Priority Data

| Apr. 28, 1978 [JP] | Japan | 53/51650 |
| Apr. 28, 1978 [JP] | Japan | 53/51663 |
| Apr. 28, 1978 [JP] | Japan | 53/51664 |
| Apr. 28, 1978 [JP] | Japan | 53/51680 |

[51] Int. Cl.³ .................................................. G01N 21/26
[52] U.S. Cl. ......................................... 356/435; 250/565; 356/442
[58] Field of Search ............. 356/435, 436, 434, 433, 356/440, 441, 442; 250/573, 575, 576, 564, 565

[56] References Cited

U.S. PATENT DOCUMENTS

| 3,114,253 | 12/1963 | Morey et al. | 60/12 R |
| 3,954,342 | 5/1976 | Boeke | 356/435 |
| 3,976,891 | 8/1976 | Parkinson | 250/575 |
| 4,003,661 | 1/1977 | Yamano | 356/436 |
| 4,037,973 | 7/1977 | Carr | 356/435 |

*Primary Examiner*—Richard A. Rosenberger
*Attorney, Agent, or Firm*—Oblon, Fisher, Spivak, McClelland & Maier

[57] ABSTRACT

The apparatus for measuring the degree of rinsing for use in a washing machine is provided with a source of light, a first phototransistor disposed to receive light emitted by the light source for producing a reference signal, a second phototransistor disposed to receive the light from the light source for producing a measuring signal corresponding to the amount of light received and a calculating circuit for arithmetically operating the reference signal and the measuring signal for producing an output signal corresponding to the relative values of the reference signal and the measuring signal. A first optical path between the light source and the first phototransistor and a second optical path between the light source and the second phototransistor are both disposed in rinsing water and the length of the first optical path is set to be longer than the length of the second optical path.

9 Claims, 7 Drawing Figures

F I G. 5A 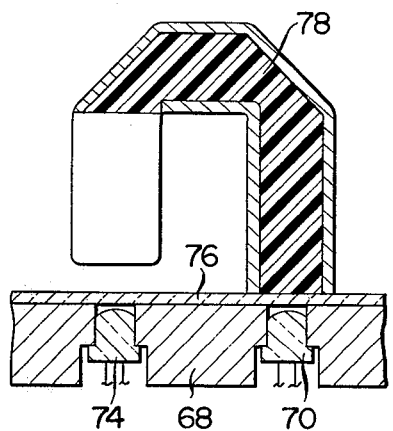
F I G. 5B 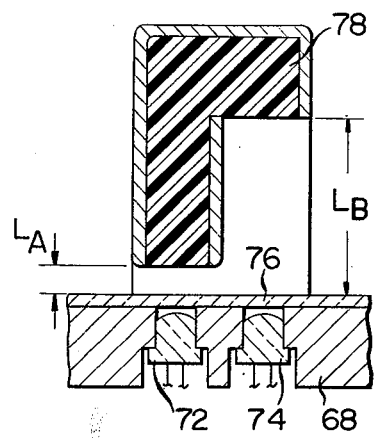
F I G. 6 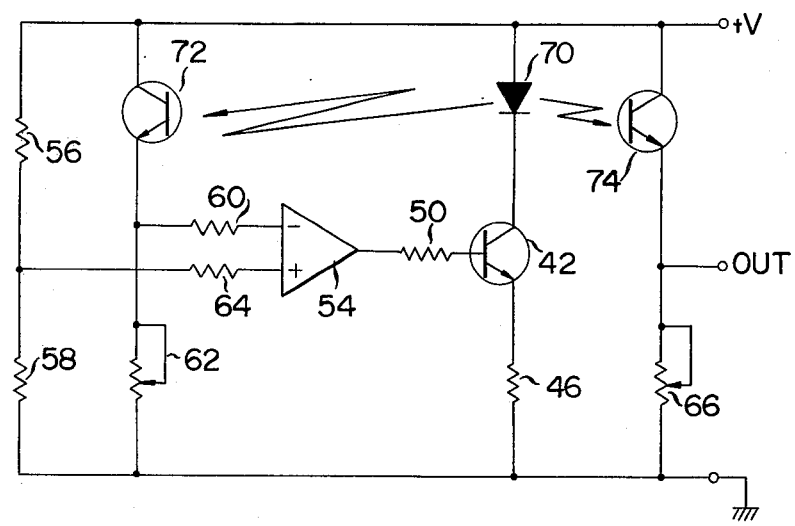

APPARATUS FOR MEASURING THE DEGREE OF RINSING

This invention relates to apparatus for measuring the degree of rinsing of a washing machine.

It is a recent trend to automate various steps of the operation of a washing machine. Since the periods of respective steps are predetermined by a timer or the like, when the amount of clothes to be washed is small or they are not so much spoiled the periods are excessive. Especially at the final stage of the rinsing step, so-called overflow rinsing is performed in which the washed clothes are rinsed while pouring water into a washing tub and drain the rinsing water, so that if rinsing is performed too long not only electric power but also water are wasted. Accordingly, in order to save electric power and water it is important to accurately measure the degree of rinsing of the washed clothes during the rinsing step. The degree of rinsing is expressed by the extent of the amount of light transmitting through the water after rinsing approaches that of light transmitting the water before rinsing. The amount of the transmitting light is determined not only by the degree of turbidity of the rinsing water but also by the amount of the bubbles formed by the bubble detergent dissolved in the washing water. At present, since bubble detergents are generally used as the detergents for washing, bubbles are produced by the detergent remaining in the rinsing water due to the relative motion between the rinsing water and washed clothes during the rinsing step whereby light is scattered to decrease the amount of the transmitting light. For this, reason, the fact that the water after rinsing becomes clear does not mean completion of the rinsing, and only when the bubble due to the residual detergent becomes nearly zero the rinsing is completed.

One example of the prior art apparatus for measuring the degree of rinsing is disclosed in U.S. Pat. No. 3,114,253 wherein a light emitting element and a light receiving element are disposed in a washing tub to measure the amount of light transmitting though the rinsing water. When used over a long time, the light emitting and light receiving surfaces become dirty and the amount of the emitted light is caused to vary due to this fact and the variation of the characteristic of the light emitting element caused by temperature variation. Therefore, where the amount of the transmitting light is determined by the amount of the received light, the resulting value is not accurate. To prevent this, it has been necessary to rely upon manual correction (clearing of the light emitting and receiving surfaces) or to use complicated correction and calculating circuit.

To measure relative amount of the transmitting light, a spectrophotmeter has been proposed wherein a sample liquid to be measured is put in a measuring cell having two optical paths of different path length and in which the amount of light transmitting though shorter optical path is used as a reference (see Japanese Patent Publication No. 37792 of 1977). In this manner, when the sample liquid to be measured is contained in the measuring cell, the bubbles in the rinsing water are difficult to enter the measuring cell. Even when the bubbles enter the cell, the bubbles in the cell rapidly rise to the upper portion of the cell because the water in the cell is not stirred, so that in some cases the bubbles would be moved out of the optical path. For this reason, such device can not measure the amount of the bubbles of the rinsing water.

Accordingly, it is an object of this invention to provide apparatus for measuring the degree of rinsing capable of measuring the degree of rinsing of washed clothes by measuring the amount of light transmitting through the rinsing water based on the degree of turbidity of the rinsing water and the amount of bubbles due to residual detergent.

Another object of this invention is to provide apparatus for measuring the degree of rinsing capable of readily compensating for the variation in the amount of the measuring light caused by aging or variation in the temperature characteristics of the light emitting element and the light receiving element.

A further object of this invention is to provide apparatus for measuring the degree of rinsing so constructed that the amount of light intercepted by thrums of the washed clothes and the bubbles generated by residual detergent is small thus decreasing measuring error.

According to this invention these and further objects can be accomplished by providing apparatus for measuring the degree of rinsing for use in a washing tub containing clothes to be washed and liquid in which a bubble detergent is dissolved and including means for relatively moving the clothes and the liquid, the apparatus comprising a source of light arranged to transmit light through the liquid, a first photoelectric converting element disposed to receive light emitted by the light source and passed through the liquid dissolved a bubble detergent for producing a first output signal corresponding to the amount of light received, a second photoelectric converting element for receiving the light emitted by the light source to produce a second output signal corresponding to the amount of light received, the second photoelectric converting element being located at such position that the path length of a optical path in the liquid between the light source and the second photoelectric converting element is longer than the length of a optical path in the liquid between the light source and the first photoelectric converting element, and calculating means which arithmetically operates the second output signal by using the first output signal as a reference thereby producing a calculated signal corresponding to the amount of the light transmitting through the liquid.

In the accompanying drawings:

FIGS. 5A and 5B are sectional views showing a modified embodiment of this invention; and FIG. 6 is a connection diagram of the modified embodiment shown in FIGS. 5A and 5B.

Figure 1:
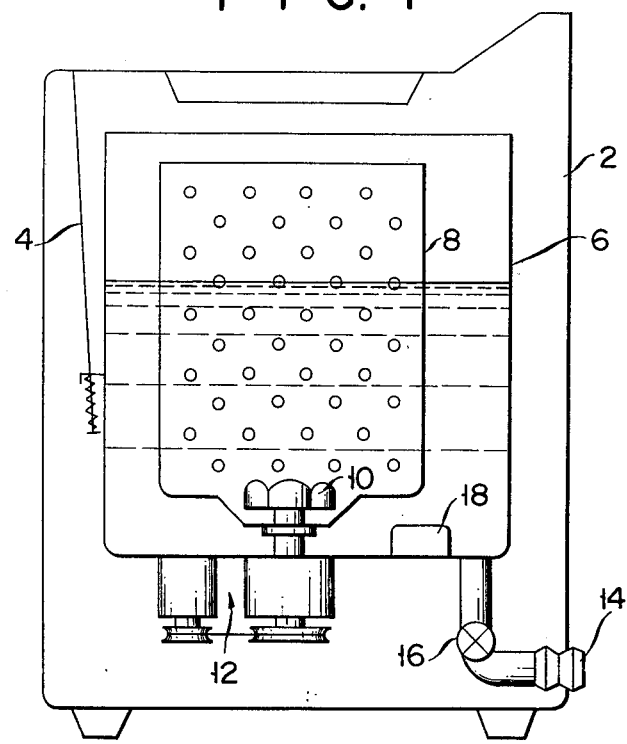
FIG. 1 is a diagrammatic representation of a washing machine as a whole.

At first a washing machine to which the apparatus of this invention is applicable will be described. As shown in FIG. 1, a washing tub 6 is resiliently supported by a box 2 by means of resilient supporting members 4, and a rotatable dehydration tub 8 is arranged in the washing tub 6. The peripheral wall of the dehydration tub 8 is provided with numerous perforations, and a stirring blade 10 is secured to the bottom of the dehydration tub 8. An electric motor 12 is mounted under the washing tub 6 to drive the stirring blade 10 and the dehydration tub 8. A drain pipe 14 including a drain valve 16 is connected to the bottom of the washing tub 6. The apparatus of this invention 18 for measuring the degree of rinsing is also mounted on the bottom of the washing tub 6.

With the washing machine of the type described above, during the washing step, the drain valve 16 is closed. After supplying water into the washing tub 6, the motor 12 drives the stirring blade 10 to stir the clothes to be washed and the washing water to wash the clothes. During the dehydration step, the drain valve 16 is opened to discharge the water in the washing tub 6 to the outside and then the dehydration tub 8 is rotated at a high speed by the motor 12 to squeeze water contained in the washed clothes in the dehydration tub 8 by centrifugal force. The squeezed water is discharged though peripheral perforations. At the first stage of the rinsing step, the same operation as in the washing step is repeated, except that rinsing water is supplied into the washing tub 6. During the last stage of the rinsing step, i.e. during the overflow rinsing step, the drain valve 16 is opened to discharge the water while at the same time the stirring blade 10 is rotated by motor 12 to rinse the washed clothes by stirring them with the rinsing water. The various steps described above are performed automatically by a well known control device including an electronic timer. Since an electronic timer utilizing a microcomputer is well known in the art, it is believed unnecessary to describe it herein. During the rinsing step, when the degree of rinsing reaches a predetermined degree as measured by the apparatus for measuring the degree of rinsing, the step is advanced to the next step.

Figure 2:
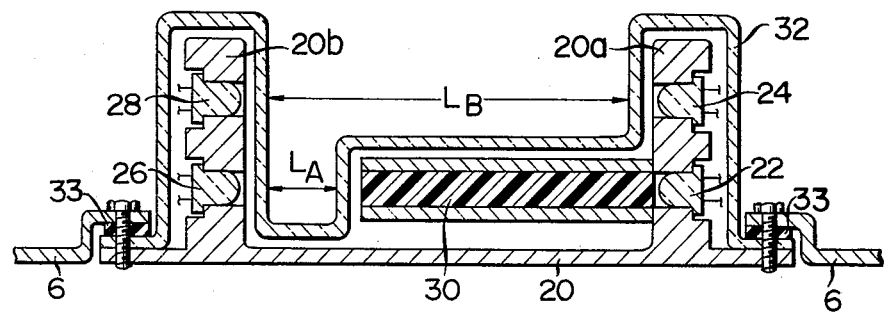
FIG. 2 is a longitudinal sectional view showing one example of the apparatus for measuring the degree of rinsing embodying the invention.
Figure 3:
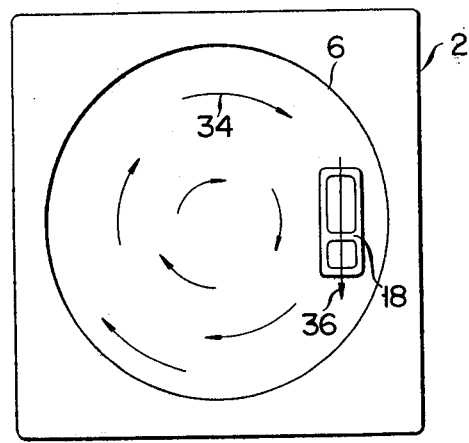
FIG. 3 is a plan view showing a manner of arranging the measuring apparatus.

As shown in FIG. 2, the measuring apparatus comprises a base plate 20 having integral pedestals 20a and 20b near its opposite ends. Light emitting diodes (which is reffered to as LED) 22 and 24 acting as the light emitting elements are disposed in openings through one pedestal 20a where as phototransistors (which is reffered to as PTR) 26 and 28 acting as the light receiving elements are disposed in openings through the other pedestal 20b. LED 22 and 24 and PTR 26 and 28 form a pair of optical paths and in the first optical path a light guide 30 is disposed contiguous to the LED 22. The light guide 30 is made of an acrylic resin member coated with a layer of aluminum plating so that it can transmit the light emitted by the LED 22 without any appreciable attenuation. Thus, the first and second optical paths are shielded with each other. The light guide, the LED and the PTR are covered by a water tight casing 32 contoured to follow their, configurations. The casing is made of such transparent materials as acrylic resins or the like, and all corners are rounded, thus preventing the thrums from depositing on the measuring apparatus. Even when foreign matters deposite on the light emitting and light receiving surfaces, they are readily removed by the vibration of the washing tub 6 caused by the rotation of the dehydration tub 8 at the time of dehydration, thus preventing measuring error caused by the variation in the amount of the transmitting light. The measuring apparatus is mounted in an opening at the bottom of the washing tub 6 in a water tight fashion through a rubber packing 33. FIG. 3 shows the relative position of the measuring apparatus at the bottom of the washing tub 6, in which arrow 34 shows the direction of flow of the rinsing water, which arrow 36 the direction of the transmitting light of the measuring apparatus. In an automatic reversing type washing machine, the water also flows in a direction opposite to that of arrow 34. In any case, the measuring apparatus 18 is disposed such that its optical paths are directed in the same direction as the direction of flow of the rinsing water. This prevents the thrums contained in the flow of the rinsing water from flowing across the optical paths of the measuring apparatus 18 thereby preventing accidental measuring error described above. Furthermore, the bubbles generated by the residual detergent and caused by the rotation of the stirring blade during the rinsing step is fine and uniformly distributed at the lower portion of the washing tub 6, so that deposition of the measuring apparatus at the bottom thereof permits measurement of the amount of bubbles thus assuming accurate measurement of the degree of rinsing. When the measuring apparatus is disposed at a corner of the washing tub 6, as the rinsing water is not strongly stirred, it is impossible to measure the amount of bubbles generated by the residual detergent. As a consequence, it is advantageous to locate the measuring apparatus at a position remote from the corner in order to accurately measure the amount of the bubbles, that is the residual detergent.

Figure 4:
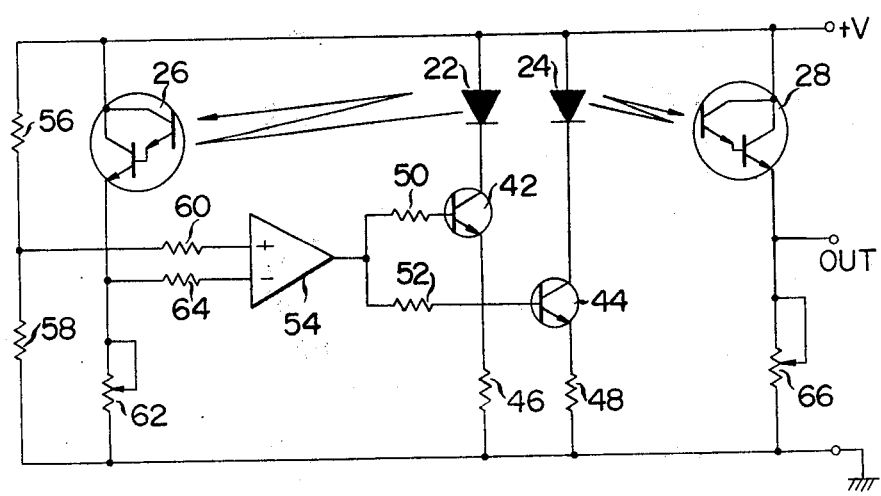
FIG. 4 is an electric connection diagram of the measuring apparatus.

FIG. 4 shows the electric circuit of the apparatus for measuring the degree of rinsing described above. The LED and the PTR are designated by the same reference characters as in FIG. 2. The anode electrodes of the LED 22 and 24 are connected to the positive side $+V$ of the source whereas the cathode electrodes are respectively connected to the collector electrodes of transistors 42 and 44 so as to be lighted by these transistors. The emitter electrodes of these transistors are grounded respectively through resistors 46 and 48 and their base electrodes are connected to be driven by an operational amplifier 54 through resistors 50 and 52 respectively. A reference voltage derived from the juncture between potentiometer resistors 56 and 58 connected across the source is applied to the noninverting input $(+)$ of the operational amplifier 54 through an input resistor 60. The PTR 26 which constitutes the first optical path together with the LED 22 is of the Darlington type and its collector electrode is connected to the positive side of the source $+V$ while the emitter electrode is connected to the ground through a trimmer resistor 62. The voltage across the trimmer resistor 62, that is the voltage corresponding to the amount of light received the PTR 26 is applied to the inverting input $(-)$ of the operational amplifier 54 through an input resistor 64. In this manner, a photo-coupler constituted by the LED 22 and the PTR 26 comprises a feedback circuit for the operational amplifier. The second PTR 28 which receives the light emitted by the second LED 24 is also of the Darlington type and its collector electrode is connected to the positive side of the source while the emitter electrode is grounded through a trimmer resistor 66. The voltage across this resistor, that is the voltage corresponding to the amount of light received by the second PTR 28 appears at the output terminal out.

Since a light guide 30 is disposed in the first optical path (between LED 22 and PTR 26) in the rinsing water, the length of the first optical path $L_A$ is shorter than the length $L_B$ of the second optical path as shown in FIG. 2. Consequently, the attenuation of the light is greater in the second optical path than in the first optical path so that when both LED 22 and 24 emit the same amount of light, the first PTR 26 would receive much more amount of light than the second PTR 28.

Accordingly, the amount of light received by the second PTR 28 relative to the amount of light received by the first PTR 26, which is taken as the reference, represents the percentage of light transmission of the rinsing water.

Generally, the percentage of light transmission in two optical paths having different path length can be expressed as follows according to the law of Lambert Beer $$T_R = 10^{\{2-(2-\log T_S)\frac{L_A}{L_B}\}}$$

where $T_R$ and $T_S$ represents the percentage of light transmission of the first and second optical paths respectively.

In order to minimize the effect of the variation in the percentage of light transmission of the first optical path which is taken as a reference of measurement it is necessary to make large the ratio $L_A$ to $L_B$. In this embodiment, this ratio is selected to be $L_A:L_B=1:10$. Since the measuring apparatus is disposed in the washing tub the maximum value of $L_B$ is about 100 mm while the minimum value of $L_A$ should be 4 mm when one considers the presence of the bubbles and thrums. Thus, the maximum ratio is 1:25.

The following Table shows measured values and the theoretical values for demonstrating the accuracy of the measuring apparatus.

| Measured value $T_R$ | | Measured value $T_S$ | | Relative percentage of transmission | Theoretical value | |
|---|---|---|---|---|---|---|
| voltage [V] | % of transmission | voltage [V] | % of transmission | $T_S'[\%T]$ | $T_R'[\%T]$ | $T_S''[\%T]$ |
| 3.92 | 100.0 | 4.00 | 100.0 | 100.0 | 100.0 | 100.0 |
| 3.90 | 99.5 | 3.91 | 97.8 | 98.3 | 99.8 | 98.0 |
| 3.81 | 97.2 | 3.60 | 90.0 | 92.6 | 99.0 | 90.9 |
| 3.77 | 96.2 | 3.19 | 79.8 | 83.0 | 97.8 | 81.6 |
| 3.73 | 95.2 | 2.90 | 72.5 | 76.2 | 96.8 | 74.9 |
| 3.63 | 92.6 | 2.52 | 63.0 | 68.0 | 95.5 | 66.0 |
| 3.58 | 91.3 | 2.25 | 56.3 | 61.7 | 94.4 | 59.6 |
| 3.48 | 88.8 | 1.793 | 44.8 | 50.5 | 92.3 | 48.5 |
| 3.36 | 85.7 | 1.383 | 34.6 | 40.4 | 89.9 | 38.5 |
| 3.23 | 82.4 | 0.946 | 23.7 | 28.8 | 86.6 | 27.4 |
| 3.01 | 76.8 | 0.622 | 15.6 | 20.3 | 83.0 | 18.8 |
| 2.76 | 70.4 | 0.332 | 8.3 | 11.8 | 78.0 | 10.6 |
| 2.51 | 64.0 | 0.159 | 4.0 | 6.3 | 72.5 | 5.5 |
| 1.90 | 48.5 | 0.043 | 1.1 | 2.3 | 63.7 | 1.7 |
| 0.497 | 12.7 | 0 | 0 | 0 | 0 | 0 |

In this table, the measured values $T_R$ and $T_S$ represent the amounts of the light when the same amount of light is emitted by the first and second optical paths having different length (the ratio of the length of the first and second light paths being 1:10). In each of the measured values of $T_R$ and $T_S$, the left column represent voltage corresponding to the amount of received light and right column the percentage of light transmission. As shown, the percentage of light transmission of the first optical path $T_R$ having shorter length is stable, that is higher than about 80% T regardless of substantial variation (100% T ~ 10% T) in the percentage of light transmission of the second optical path $T_S$ having longer length. $T_S'$ represents the relative percentage of light transmission of the second optical path having longer length and this value of $T_S'$ ($T_S'=(T_S/T_R)\times 100$) appears as the output of the measuring apparatus. It is to be understood that the amount of light emitted by the first LED 22 is controlled by the operational amplifier 54 such that the amount of light received by the first PTR 26 would be constant. As above described, since the first LED 22 and the first PTR 26 constitute a feedback circuit for the operational amplifier 54, as the amount of the light received by the PTR 26 decreases, the amount of light emitted by the LED 22 would be increased by the operation of the operational amplifier 54. The emitter electrodes of PTR 26 and 28 are connected to trimmer resistors 62 and 66 respectively so as to variably set their output levels. As a consequence, where the trimmer resistors 62 and 66 are respectively adjusted to make the output to be 100% T after the water has filled in the washing tub 6, the output would represent the percentage of light transmission $T_S'$ (degree of rinsing) of the rinsing water, by taking the percentage of light transmission of the first (reference) optical path as 100% T.

The theoretical value $T_R'$ shown in the Table is obtained by instituting the measured value $T_S$ in the equation of Lambert Beer. The theoretical value $T_S''$ represents the relative percentage of light transmission of the second optical path calculated by using $T_R'$ thus determined. Thus, $$T_S''=(T_S/T_R')\times 100,$$

where $$L_A/L_B=1/10.$$

As above described, the measured value of $T_S$ of the percentage of light transmission of the rinsing water is different only 4% from the relative percentage of light transmission $T_S'$, when the percentage of light transmission of the first optical path $T_R$ of about 80% T is taken as the reference. In addition, the relative percentage of light transmission $T_S'$ differs only 2% from the theoretical value $T_S''$. Furthermore, since the rinsing water to be measured flows across both the first optical path (used as the reference) and the second optical path, attenuation of the amount of light through the optical paths caused by turbidity of the light emitting and receiving surfaces does never affect the accuracy of the measurement. When the percentage of light transmission exceeds a definite value, for example about 80%, it is judged that the rinsing has been completed and a step advance signal is sent to a control circuit. When thrums or other foreign matters intercept the optical path, an abnormal signal is generated and the control circuit continues the rinsing operation for a predetermined interval.

The invention is not limited to the embodiment described above. In the following a modified embodiment will be described. FIG. 5A shows a sectional view as viewed from the second optical path, FIG. 5B is a sectional view as viewed from the light receiving element and FIG. 6 is a connection diagram of the modified embodiment. As shown, a LED 70 and first and second PTR 72 and 74 are inserted in the openings provided for a base plate 68. In FIG. 5A, the first PTR 72 is not seen, because it is located behind the second PTR 74, a transparent plate 76, made of acrylic resin, for example, is bonded to the upper surface of the base plate 68 for maintaining such circuitries as the LED and PTR in a water tight condition, a light guide 78 is mounted on the transparent plate 76. The end of the light guide 78 opposite to the mounted end is cut at an angle of 45° so as to reflect light and cause it to travel in parallel with the base plate 68. The end surface is cut again at an angle of 45° above the phototransistor 74 to reflect the light thereto. The light emitted by the LED 70 is directed to both PTR. The light exit surface of the light guide 78 for the first PTR 72 is located close to the base plate 68, whereas the light exit surface of the light guide for the second PTR 74 is located remote from the base plate 68. More specifically the length $L_A$ in the rinsing water of the first optical path defined by the LED 70 and the first PTR 72 is set to be shorter than the length $L_B$ in the rinsing water of the second optical path defined by the LED 70 and the second PTR 74. Moreover, as the corners of the light guide 78 is rounded, it is difficult for the thrums or other foreign matters from depositing thereon.

In FIG. 6 elements corresponding to those shown in FIG. 4 are designated by the same reference characters and their description is omitted. The modification shown in FIG. 6 is different from the embodiment shown in FIG. 4 in that the luminous element comprises only one LED so that there is an advantage that there is no measurement error caused by the difference between the characteristics of two luminous elements, which is inevitable in the embodiment shown in FIG. 4.

It should be understood that the invention is not limited to the specific embodiments described above. Thus, for example, the light guide may be formed of optical fibers and the light emitting and receiving elements may comprise lamps or solar cells or Cds elements.

What is claimed is:

1. An apparatus for measuring the degree of rinsing for use in a washing tub containing clothes to be washed and liquid in which a bubble detergent is dissolved and including stirring means for relatively moving said clothes and liquid, said apparatus comprising:

a light source disposed at the bottom of the washing tub to transmit light through the liquid;

a first photoelectric converting element disposed at the bottom of the washing tub to receive light emitted by said light source and having an optical path in said liquid for producing a first output signal corresponding to the amount of light received;

a second photoelectric converting element disposed at the bottom of the washing tub to receive light emitted by said light source and having an optical path in said liquid to produce a second output signal corresponding to the amount of light received, said second photoelectric converting element being located at such position that the length of the optical path in said liquid between said light source and said second photoelectric converting element is longer than the length of the optical path in said liquid between said light source and said first photoelectric converting element;

circuit means including feedback means connected between said first photoelectric converting element and said light source so as to control the amount of light emitted thereby such that said first output signal will be constant; and whereby said second output signal corresponds to the amount of said light transmitted through said liquid.

2. The measuring apparatus according to claim 1, wherein said first and second photoelectric converting elements are disposed such that said optical paths between these elements and said light source are parallel with each other.

3. The measuring apparatus according to claim 1, wherein said first and second photoelectric converting elements are disposed such that said optical paths between said elements and said light source are in the same direction as the direction of flow of said liquid stirred by said means.

4. The measuring apparatus according to claim 1, wherein said first and second photoelectric converting elements respectively comprise phototransistors.

5. The measuring apparatus according to claim 4, wherein said light source comprises two light emitting diodes.

6. The measuring apparatus according to claim 4, wherein said light source comprises a single light emitting diode.

7. The measuring apparatus according to claim 6, wherein said single light emitting diode is disposed at one end part of a base plate, said two phototransistors are disposed on the other end part of said base plate to oppose each other, and wherein a light guide is interposed between said light emitting diode and one of said phototransistors, and a transparent cover with rounded corner is water tightly mounted on said base plate and single light emitting diode and two phototransistors.

8. The measuring apparatus according to claim 5, wherein said two light emitting diodes are disposed at one end part of a base plate and said two phototransistors are disposed at the other end part of said base plate, and wherein a light guide is interposed between one of said light emitting diodes and one of said light emitting diodes, and a transparent cover with rounded corners is water tightly mounted on said base plate and two light emitting diodes and two phototransistors.

9. The measuring apparatus according to claim 1, wherein said feedback means includes a generator for generating a reference signal, a comparator connected to said first photoelectric converting element and generator for producing a comparison signal according to the comparison between the first output signal and the reference signal and a driver connected to said comparator and light source for driving said light source according to the comparison signal.

* * * * *